United States Patent
Chodkowski

(10) Patent No.: US 10,369,314 B2
(45) Date of Patent: Aug. 6, 2019

(54) CUSTOMIZABLE CUSHION UTILIZING FITTED PLUG INSERTS

(71) Applicant: KONINKLIJKE PHILIPS N.V., Eindhoven (NL)

(72) Inventor: Lauren Patricia Chodkowski, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1135 days.

(21) Appl. No.: 14/431,310

(22) PCT Filed: Sep. 26, 2013

(86) PCT No.: PCT/IB2013/058888
§ 371 (c)(1),
(2) Date: Mar. 26, 2015

(87) PCT Pub. No.: WO2014/053966
PCT Pub. Date: Apr. 10, 2014

(65) Prior Publication Data
US 2015/0238719 A1    Aug. 27, 2015

Related U.S. Application Data

(60) Provisional application No. 61/708,659, filed on Oct. 2, 2012.

(51) Int. Cl.
*A61M 16/06* (2006.01)

(52) U.S. Cl.
CPC ........ *A61M 16/0622* (2014.02); *A61M 16/06* (2013.01); *A61M 16/0616* (2014.02); *A61M 2016/0661* (2013.01)

(58) Field of Classification Search
CPC .............. A61M 16/0622; A61M 16/06; A61M 2016/0661
See application file for complete search history.

(56) References Cited

U.S. PATENT DOCUMENTS

| | | | | | |
|---|---|---|---|---|---|
| 2,157,826 | A | * | 5/1939 | Kearney | A01L 1/04 168/13 |
| 4,916,765 | A | * | 4/1990 | Castronovo, Jr. | A47G 9/1081 297/284.1 |
| 6,467,483 | B1 | * | 10/2002 | Kopacko | A61M 16/06 128/205.25 |

(Continued)

FOREIGN PATENT DOCUMENTS

| EP | 1116492 A2 | 7/2001 |
|---|---|---|
| WO | WO2004041342 A1 | 5/2004 |
| WO | WO2012025843 A1 | 3/2012 |

*Primary Examiner* — Gregory A Anderson
*Assistant Examiner* — Victoria Murphy
(74) *Attorney, Agent, or Firm* — Michael W. Haas

(57) ABSTRACT

A respiratory interface device provides a support cushion (15) including a cushion body (20) and at least two inserts (50). The cushion body has a plurality of stiffener passages (22). The at least two inserts are stiffening inserts shaped to correspond to the stiffener passages. The cushion body is made from a first material having a first hardness. One of the at least two inserts is made from a first material, having substantially the same first hardness as the cushion body, and the second insert is made from a second material having a second hardness, the second hardness being different than the first hardness.

20 Claims, 4 Drawing Sheets

(56) References Cited

U.S. PATENT DOCUMENTS

| | | | |
|---|---|---|---|
| 2003/0145859 A1* | 8/2003 | Bohn | A61M 16/06 128/206.24 |
| 2006/0032504 A1* | 2/2006 | Burton | A61M 16/06 128/207.11 |
| 2008/0257354 A1* | 10/2008 | Davidson | A61M 16/06 128/206.24 |
| 2008/0289633 A1 | 11/2008 | Kwok | |
| 2010/0006101 A1* | 1/2010 | McAuley | A61M 16/06 128/206.24 |
| 2010/0024811 A1* | 2/2010 | Henry | A61H 9/0078 128/202.16 |
| 2011/0088699 A1 | 4/2011 | Skipper | |
| 2011/0174310 A1 | 7/2011 | Burz | |
| 2012/0132208 A1 | 5/2012 | Judson | |

* cited by examiner

US 10,369,314 B2

CUSTOMIZABLE CUSHION UTILIZING FITTED PLUG INSERTS

CROSS-REFERENCE TO RELATED APPLICATIONS

This patent application claims the priority benefit under 35 U.S.C. § 371 of international patent application No. PCT/IB2013/058888, filed Sep. 26, 2013, which claims the priority benefit under 35 U.S.C. § 119(e) of U.S. Provisional Application No. 61/708,659 filed on Oct. 2, 2012, the contents of which are herein incorporated by reference.

BACKGROUND OF THE INVENTION

1. Field of the Invention

The present invention relates to respiratory interface devices for transporting a gas to and/or from an airway of a user which include, but not limited to, a mask having a flexible faceplate or patient contacting cushion, and, in particular, to a flexible faceplate or patient contacting cushion having a selectable hardness by virtue of removable inserts.

2. Description of the Related Art

Respiratory interface devices, such as a mask, may include a relatively rigid faceplate and a softer patient contacting cushion. Alternatively, a flexible faceplate may act as a patient contacting cushion. Hereinafter, this description shall refer to a patient contacting cushion but it is understood that the patient contacting cushion may be a flexible faceplate as well. The patient contacting cushion is made from a relatively soft material that is structured to substantially adapt to the contour of the user's face. Thus, the patient contacting cushion creates a generally continuous seal about the user's nose and/or mouth.

While such patient contacting cushions create a generally continuous seal, the seal may include gaps or may be subject to gapping when the user moves. Such gapping may be caused by the patient contacting cushion being too soft, or too soft in a specific location.

SUMMARY OF THE INVENTION

One embodiment of the present invention provides a respiratory interface device support cushion including a cushion body and at least two inserts. The cushion has a peripheral contour and the cushion body has a cross-sectional shape generally similar to the mask peripheral contour. The cushion body further defines a passage. The cushion body has an distal member, a sidewall, and a proximal member. The cushion body distal member and cushion body proximal member are maintained in a spaced relation by the cushion body sidewall. The cushion body sidewall has an inner side and an outer side. The cushion body sidewall also has a plurality of stiffener passages. The passages may be axial or radial passages. The at least two inserts are stiffening inserts shaped to correspond to the plurality of stiffener passages. The cushion body is made from a first material having a cushion body hardness. One of the at least two inserts is made from the first material, having a first hardness and the second insert is made from a second material having a second hardness, the second hardness being different than the first hardness. In one embodiment, the insert first hardness is substantially the same hardness as the cushion body. Alternatively, both inserts may be of a different hardness than cushion body. In use, one insert is inserted into each of the plurality of stiffener passages and the selection of the insert as being of the first material or the second material selectively determines the localized hardness of the cushion.

It is a further object of this invention to provide a method of using a respiratory interface device support cushion described above, the method including the steps of inserting one insert in each at least one stiffener passage, and, positioning the mask over the user's face.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
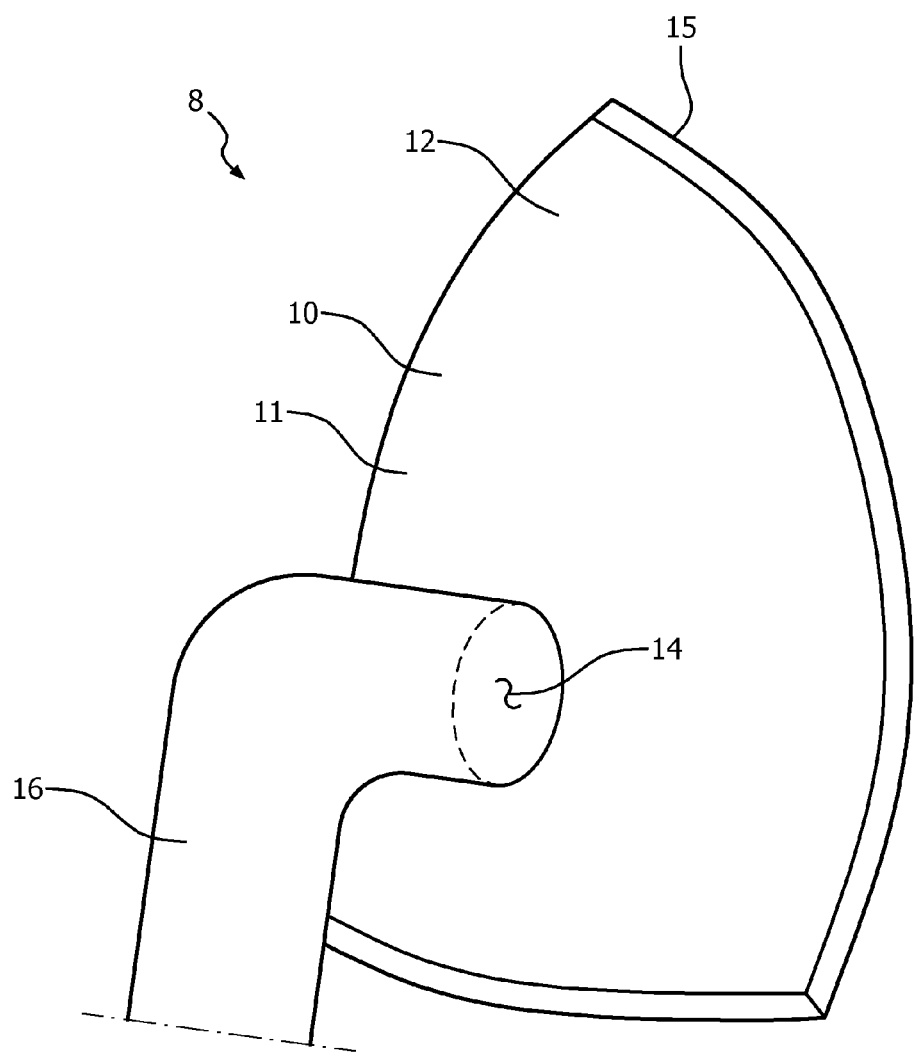
FIG. 1 is an isometric view of a respiratory interface device mask.

As used herein, the singular form of "a", "an", and "the" include plural references unless the context clearly dictates otherwise. As used herein, the statement that two or more parts or components are "coupled shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall means that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, "a generally continuous seal" may have a gap or may gap when the user moves. As used herein, "a more complete seal" has a gap that is shorter in length than a gap of a generally continuous seal, or, is resistant to gapping when the user moves. As used herein, "correspond" indicates that two structural components are sized to engage each other with a minimum amount of friction. Thus, an opening which corresponds to a member is sized slightly larger than the member so that the member may pass through the opening with a minimum amount of friction. This definition is modified if the two components are said to fit "snugly" together. In that situation, the difference between the size of the components is even smaller whereby the amount of friction increases. If the element defining the opening and/or the component inserted into the opening are made from a deformable or compressible material, the opening may even be slightly smaller than the component being inserted into the opening.

FIG. 1 shows a respiratory interface device 8 according to an embodiment of the invention. In this illustrated embodiment, respiratory interface device 8 includes a respiratory mask 10. Mask 10 is coupled to a pressure generating system (not shown) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV™) device, proportional positive airway pressure (PPAP) device, C-Flex™ device, Bi-Flex™ device, or a BiPAP™ device manufactured and distributed by Philips Respironics of Murrysville, Pa., in which the pressure provided to the patient varies with the patient's respiratory cycle so that a higher pressure is delivered during inspiration than during expiration, or other pressure support device.

Respiratory mask 10 includes a body 11 with a faceplate 12 and a cushion 15, discussed below. In an exemplary embodiment, faceplate 12 is substantially rigid. In an exemplary embodiment, shown in FIG. 1, faceplate 12 is a single piece structured to cover the user's nose, mouth, or both. That is, mask 10 has a peripheral contour that is structured to extend over a user's nose and/or mouth. In this embodiment, body 11 is coextensive with faceplate 12.

It is understood that this is an exemplary embodiment and a mask may be structured to extend over just the user's nose, or, just the user's mouth. Faceplate 12 defines lower opening 14. Lower opening 14 can function as a gas inlet. Gas inlet (lower opening 14) can be coupled to a coupling device 16, such as a swivel conduit, for carrying gas such as air between mask 10 and an external gas source (not shown), such as a blower, or any other suitable device. It is contemplated that the external gas source can encompass, without limitation, any gas delivery or gas generation system capable of supplying gas for consumption by a user.

Non-limiting examples of various gas delivery therapies can include but are not limited to continuous positive airway pressure (CPAP) therapy, auto-titration positive airway pressure therapy, and bi-level positive airway pressure (BiPAP) therapy, as noted above. The particular coupling device 16, shown in FIG. 1, is not meant to be limiting and it should be understood that the present invention contemplates a variety of different coupling devices that could be attached, either permanently or selectively, to lower opening 14 to carry gas to or from mask 10. Thus, a variety of coupling devices (e.g., with or without swivels on one or both ends, and with or without an exhalation system formed integral to the device) may be substituted for coupling device 16.

Cushion 15 (FIGS. 2 and 3) is structured to extend from faceplate 12 toward the user's face and generally defines the depth of mask 10. Cushion 15 includes a cushion body 20 having at least one stiffener passage 22 and at least two inserts 50 shaped to correspond to cushion body at least one stiffener passage 22. Cushion 15 may include a sealing flap 44 (FIG. 3), discussed below. Cushion body 20 has a cross-sectional shape generally similar to mask 10 peripheral contour. Cushion body 20 defines a primary passage 24. That is, cushion body 20 is hollow and is, essentially, a shallow tube. Cushion body primary passage 24 has an axis 26.

As used herein, the terms "axial" and "radial" are used in general relation to cushion body passage axis 26. Further, while it is understood that mask 10, and therefore cushion body 20, may have any shape, a cushion body "radial" stiffener passage 22R (discussed below) is one that is disposed approximately on a line extending radially from cushion body passage axis 26 or generally parallel to such a line. For example, it is understood that cushion body "radial" stiffener passage 22R extends through the sides of a generally triangular cushion body 20, as shown, and are not always on a mathematically radial line. Similarly, a cushion body "axial" stiffener passage 22A (discussed below) is one that extends generally parallel to cushion body passage axis 26. As used herein, a cushion body "axial" stiffener passage 22A that is angled relative to a line parallel to cushion body passage axis 26 is "generally parallel to cushion body passage axis 26." Cushion body 20 may include an insert retaining device 70, discussed below.

Figure 2:
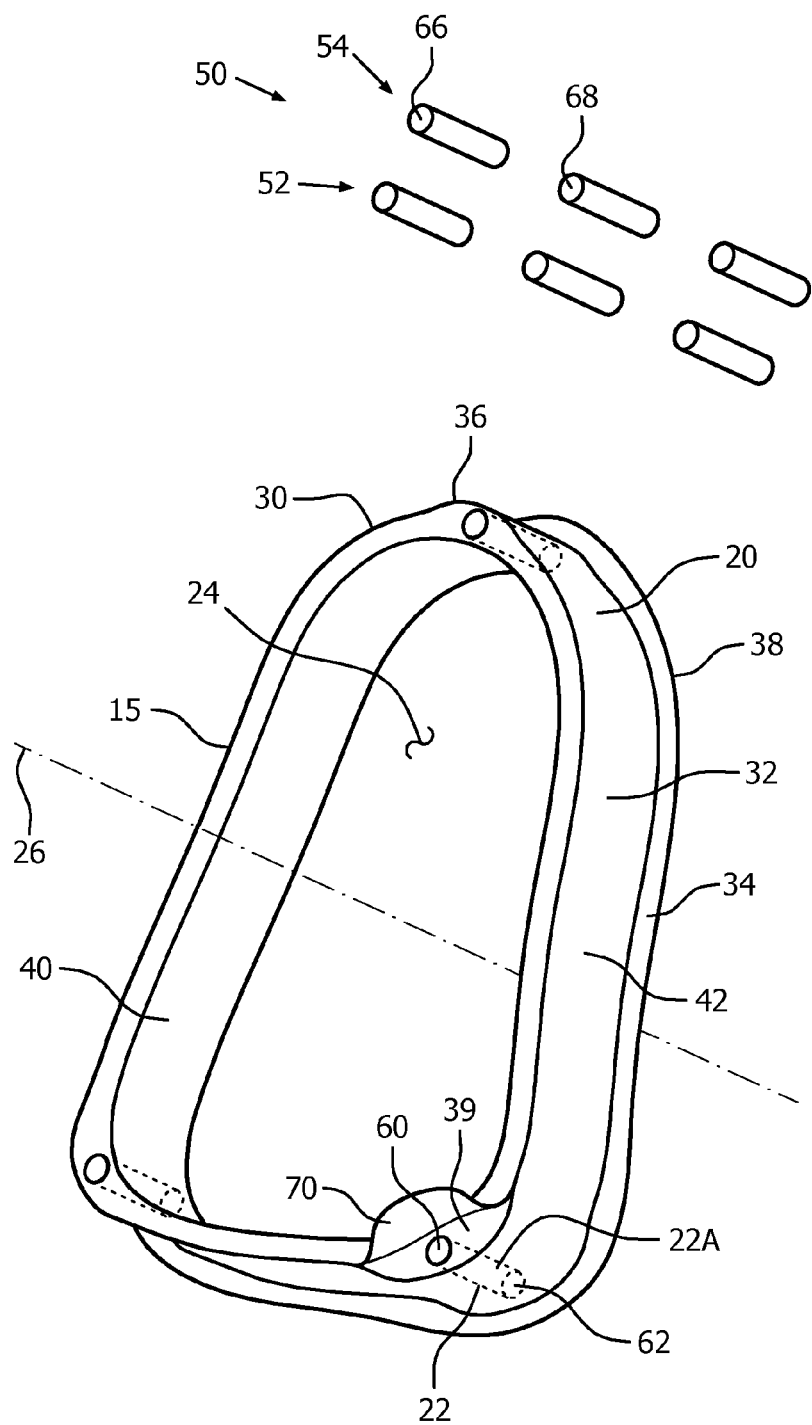
FIG. 2 is an isometric view of a cushion having axial stiffener passages.

Cushion body 20 has an distal member 30, a sidewall 32, and a proximal member 34. In reference to cushion body distal member 30 and cushion body proximal member 34, "distal" means disposed further from the user's face and "proximal" means disposed closer to the user's face. Cushion body distal member 30 and cushion body proximal member 34 may be unitary with cushion body sidewall 32. Cushion body distal member 30 and cushion body proximal member 34 may have the same cross-sectional shape as, and may be the ends of, cushion body sidewall 32. In an exemplary embodiment, however, cushion body distal member 30 and cushion body proximal member 34 have a greater cross-sectional area, but substantially the same shape as, cushion body sidewall 32. That is, as shown in FIG. 2, cushion body distal member 30 and cushion body proximal member 34 have a lip or flange 36, 38 that extends outwardly. Cushion body distal member 30 and cushion body proximal member 34 may be coupled to cushion body sidewall 32 by a hinge 39, as discussed below. Cushion body distal member 30 and cushion body proximal member 34 are maintained in a spaced relation by cushion body sidewall 26. Cushion body 20 has an inner side 40 and an outer side 42.

Cushion body proximal member 34 may be structured, i.e. contoured, to contact the user's face. In an exemplary embodiment, however, a flap 44 is structured to be coupled to cushion body proximal member 34. Flap 44 is a thin membrane of soft material structured, i.e. contoured, to contact the user's face. Flap 44 is, in an exemplary embodiment, coupled to the outer side of cushion body proximal member 34 and curves toward the inner side of cushion body proximal member 34. As discussed below, a retaining device 70 may be incorporated into flap 44. Further, as flap 44 is structured to engage the user's face and is part of cushion 15, it is understood that a description of cushion 15 contacting the user includes flap 44 contacting the user if flap 44 is in use.

Cushion body 20 is made from a generally soft, first material selected from the group including silicone, TPE. Such materials have a hardness of between about 5 shore 00 to 80 shore A. That is, cushion body 20 is made from a first material having a cushion body hardness. At least two inserts 50 are made from a generally soft, first material selected from the group including silicone, foams, TPE, polyurethane, and polypropylene, as well as similar materials. As mentioned above, and as detailed below, cushion body 20 has at least one stiffener passage 22.

An insert 50 is sized to correspond to cushion body at least one stiffener passage 22 and is structured to be inserted therein. Moreover, the characteristics of cushion 15 may be altered by providing inserts 50 of differing hardnesses. For example, if mask 10 is sized and shaped to provide a user with a more complete seal, the characteristics of mask 10, and more specifically cushion 15, may not need to be altered and insert 50 disposed in cushion body at least one stiffener passage 22 may have a hardness that is identical, or substantially similar, to the hardness of cushion body 20. If, however, mask 10 as sized and shaped provides a user with a generally continuous seal and a more complete seal is desired; then insert 50 disposed in cushion body at least one stiffener passage 22 may have a hardness that is different than the hardness of cushion body 20 thereby altering the characteristics of mask 10, and more specifically cushion 15. By altering the characteristics of mask 10, and more specifically cushion 15, mask 10 may provide a different and more complete seal for the user.

Accordingly, respiratory interface device 8 includes at least two inserts 50 are of different hardnesses and one insert 50 is disposed in each stiffener passage 22. That is, at least two inserts 50 includes at least two sets of inserts 52, 54 (FIG. 2) each set having a different hardness. That is, inserts 50 in a set 52, 54 have the same, or substantially similar, hardness but inserts 50 in different set 52, 54 have different hardnesses. If there are three sets of inserts 50 each set has a different hardness. Hereinafter only two sets 52, 54 will be discussed but it is understood that there may be more than two sets 52, 54. In an exemplary embodiment, each set 52, 54, includes an insert 50 for each stiffener passage 22. In another exemplary embodiment, each set 52, 54 includes less than one insert 50 for each stiffener passage 22, but the total number of inserts 50 in both sets 52, 54 is equal to, or greater than, the number of stiffener passages 22.

The following discussion will refer to two inserts 50 and a single stiffener passage 22. It is understood, however, that this discussion is applicable to each stiffener passage 22 in that one insert 50 out of two or more inserts 50 is disposed in each stiffener passage 22. Two inserts 50 are made from materials having different hardnesses, either a first material, having a first hardness, or, a second material having a second hardness, the second hardness being different than the first hardness. Insert 50 first hardness may be substantially the same as cushion body 20 hardness. That is, inserts 50 of first set 52 may be made from the first material, having substantially the same hardness as cushion body 20, and, inserts 50 of second set 54 are made from a second material having a second hardness, the second hardness being different than the first hardness. Alternatively, both inserts have a different hardness than cushion body 20. In an exemplary embodiment, the second hardness is greater than the first hardness. In this embodiment, use of an insert 50 from second set 54 will make cushion 15 stiffer than using an insert 50 from first set 52. Thus, use of an insert 50 made from the second material provides an increase in the localized hardness of cushion 15. Again, it is understood that while there are two inserts 50 associated with each cushion body at least one stiffener passage 22, only one insert 50 at a time is disposed therein.

Figure 3:
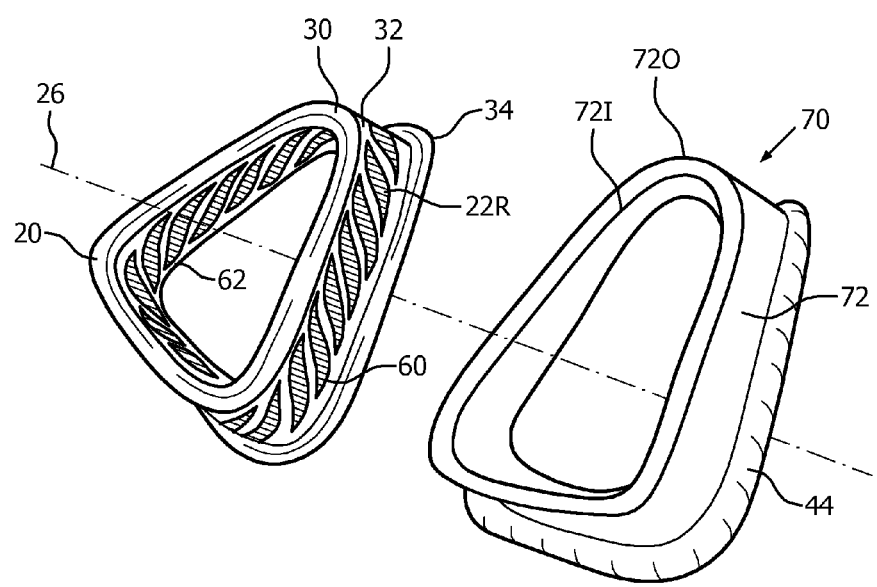
FIG. 3 is an isometric view of a cushion having radial stiffener passages.

Cushion body at least one stiffener passage 22 extends entirely through, or substantially through cushion body sidewall 32. As shown in the figures and as discussed below with regard to specific embodiments, cushion body at least one stiffener passage 22 may be either an axial stiffener passage 22A (FIG. 2) or a radial stiffener passage 22R (FIG. 3). If there is more than one cushion body stiffener passage 22, each cushion body stiffener passage 22 may have a unique shape, or, there may be a pattern of specific shapes, such as, but not limited to a repeating pattern of different shapes. Further, cushion body stiffener passages 22 may be disposed in a selected pattern, e.g. circular cushion body stiffener passages 22 adjacent corners of cushion body 20 and rectangular cushion body stiffener passages 22 therebetween. In one exemplary embodiment, shown in FIG. 4, cushion body stiffener passages 22 each have substantially the same shape.

Figure 4:
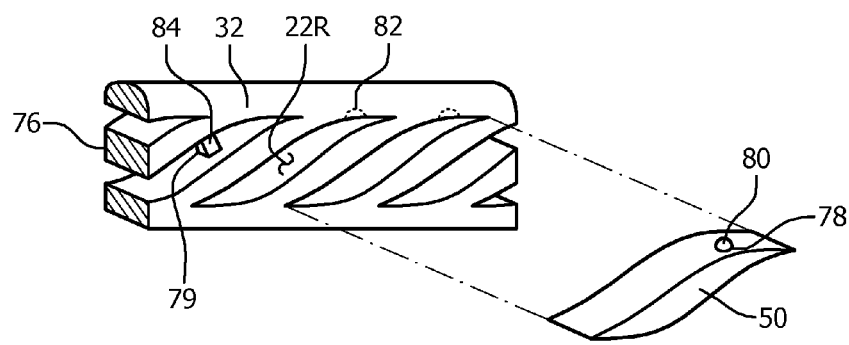
FIG. 4 is a detail view of a cushion sidewall having radial stiffener passages and various retaining devices.
Figure 5:
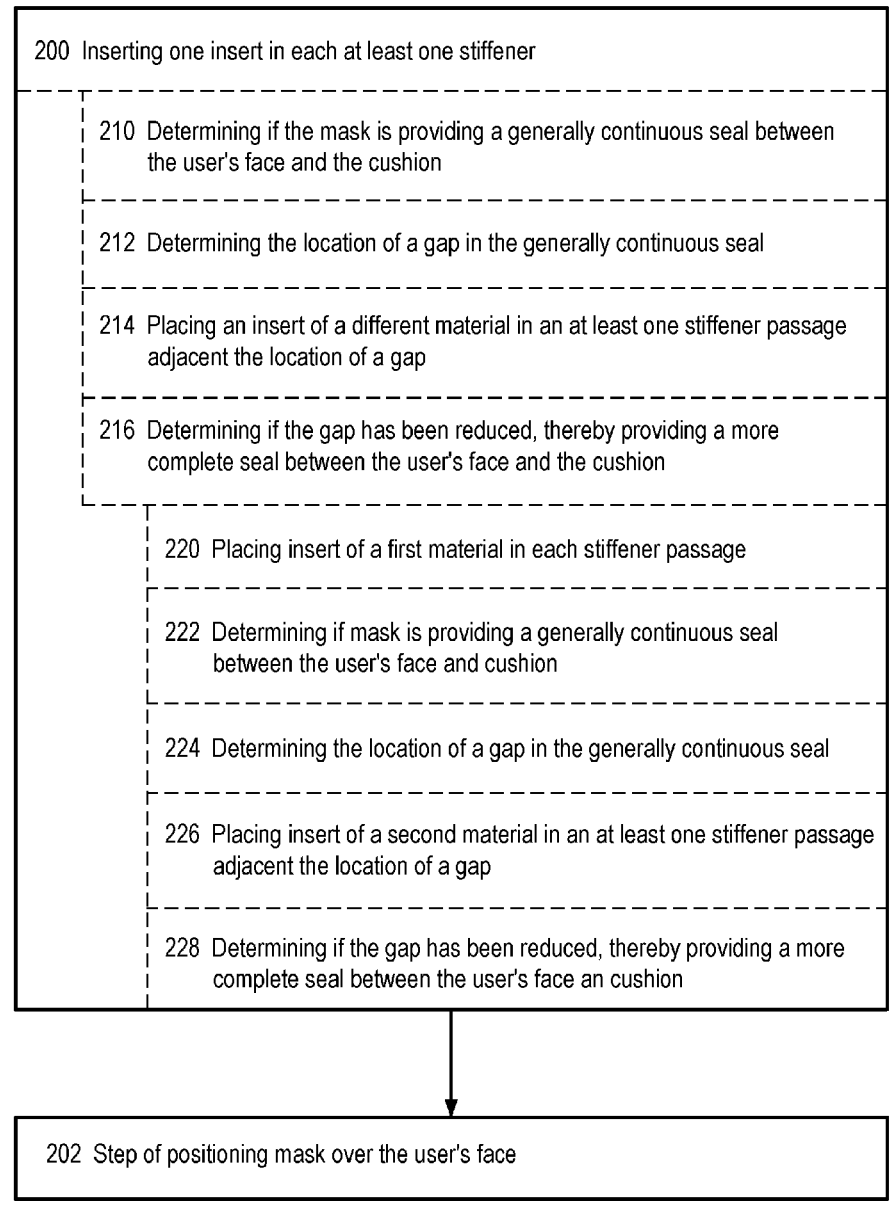
FIG. 5 is a flow chart showing the steps of the associated method.

In an exemplary embodiment, cushion body stiffener passages 22 may have a general cross-sectional shape selected from the group including circular, oval, hexagonal, rhombus, and wave. That is, it is understood that all cross-sectional shapes are generally the shape identified as opposed to exactly the shape identified. As used herein, a "wave" cross-sectional shape, as shown in FIG. 4 is a pointed oval, or vesica piscis, wherein the tips are curved. Cushion body at least one stiffener passage 22 may have a substantially continuous cross-sectional area, or, may have a tapered cross-sectional area.

As noted above, at least two inserts 50 are shaped to correspond to cushion body at least one stiffener passage 22. Thus, if cushion body at least one stiffener passage 22 is, for example, hexagonal, then both inserts 50 are hexagonal. If cushion body at least one stiffener passage 22 is, for example, tapered, then both inserts 50 are tapered. In an exemplary embodiment, each of at least two inserts 50 are sized to fit snuggly within at least one stiffener passage 22. In this embodiment, the snug fit between an installed insert 50 and at least one stiffener passage 22 acts as retaining device 70. If insert 50 is made from a compressible material, insert 50 may have a cross-sectional area that is slightly larger than at least one stiffener passage 22 and still fit snuggly within. Further, as shown in FIG. 2, inserts 50 in different sets 52, 54 may include an indicia 66 indicating to which set 52, 54 insert 50 belongs. Indicia 66 may be, but is not limited to, a mark 68 disposed on an end of insert 50. Indicia 66 may also be a color coding incorporated into, or applied to, insert 50. Further, natural differences in the material used to make inserts 50 of different sets, e.g. the materials may naturally be different colors or different shades.

Various exemplary embodiments of cushion body 20 are set forth below. It is noted that at least one stiffener passage 22, and corresponding inserts 50, may have any of the different configurations noted above. The various exemplary embodiments of cushion body 20 discussed below shall each identify a specific configuration for at least one stiffener passage 22 and corresponding inserts 50. It is understood, however, that any configuration of at least one stiffener passage 22, and corresponding inserts 50, may be used with any exemplary embodiment of cushion body 20.

In one exemplary embodiment, shown in FIG. 2, cushion body at least one stiffener passage 22 includes at least one axial stiffener passage 22A. As shown, at least one axial stiffener passage 22A includes three axial stiffener passages 22A, with one axial stiffener passage 22A disposed at each corner of a generally triangular cushion body 20. As shown, each axial stiffener passage 22A is elongated and has a generally continuous cross-section. In this embodiment, axial stiffener passages 22A extend through cushion body sidewall 32. That is, there is an opening 60, 62 to axial stiffener passage 22A adjacent both cushion body distal member 30 and cushion body proximal member 34. Further, cushion body distal member 30 and cushion body proximal member 34 are each coupled to cushion body sidewall 32 by a hinge 39, such as, but not limited to, a living hinge. In this configuration, cushion body distal member 30 and cushion body proximal member 34 may act as caps over openings 60, 62 to axial stiffener passage 22A adjacent both cushion body distal member 30 and cushion body proximal member 34. Thus, cushion body distal member 30 and cushion body proximal member 34 act as insert retaining device 70. Alternatively, axial stiffener passage 22A may extend through cushion body distal member 30 and cushion body proximal member 34.

In operation, a user selects an insert 50 from either set 52, 54 of inserts 50 for each axial stiffener passage 22A. After moving cushion body distal member 30 or cushion body proximal member 34 away from an opening 60, 62, the user inserts the selected insert 50 into each axial stiffener passage 22A via one opening 60, 62. Cushion body distal member 30 or cushion body proximal member 34 is moved over the associated opening 60, 62 thereby trapping insert 50 within axial stiffener passage 22A. The user may then use mask 10. If cushion body 20 provides a generally continuous seal and a more complete seal is desired, then an insert 50 from a different set 52, 54 may be disposed in cushion body at least one stiffener passage 22. That is, the user may swap out inserts 50 until a more complete seal is achieved. It is noted that while only two sets 52, 54 of inserts 50 have been discussed, there may be many sets each having a different hardness.

In another embodiment, shown in FIG. 3, cushion body at least one stiffener passage 22 includes at least one radial stiffener passage 22R. As shown, at least one radial stiffener passage 22R includes a plurality of radial passages 22R extending about cushion body sidewall 32. As shown, radial passages 22R have a "wave" cross-sectional shape. As described above, one insert 50 from two or more sets 52, 54 of inserts 50 is disposed in each radial passage 22R. It is noted that inserts 50 at the corners of the cushion body 20 may have a different shape than the other inserts 50. That is, the surface of corner inserts 50 may be shaped to substantially match the contour or bend of the corner.

In this embodiment, a retaining band 72 may be used as a retaining device 70. That is, retaining band 72 is structured to extend about either, or both, of the outer side and inner side of cushion body sidewall 32, thereby trapping inserts 50 within radial passages 22R. Alternatively, there may be two retaining bands 72, one structured to be disposed over the outer side of cushion body sidewall 32 and the other structured to be disposed over the inner side of cushion body sidewall 32. That is, there is an inner retaining band 72I and an outer retaining band 72O. In an exemplary embodiment, retaining band 72 is coupled to, or unitary with, flap 44. As shown, there are two retaining bands 72I, 72O that are unitary with flap 44.

In operation, a user selects an insert 50 from either set 52, 54 of inserts 50 for each radial stiffener passage 22R. The user inserts the selected insert 50 into each radial stiffener passage 22R via one opening 60, 62. Flap 44, having two retaining bands 72 is then coupled to cushion body 20 with retaining bands 72 disposed over both the outer side and inner side of cushion body sidewall 32. Thus, inserts 50 are trapped within radial stiffener passages 22R. The user may then use mask 10. If cushion body 20 provides a generally continuous seal and a more complete seal is desired; then an insert 50 from a different set 52, 54 may disposed in cushion body at least one radial stiffener passage 22R. That is, the user may swap out inserts 50 until a more complete seal is achieved.

Various retaining devices 70 are shown in FIG. 4. It is understood that multiple retaining devices 70 would not typically be used for a single cushion 15. For example, retaining device 70 may be a membrane 76 disposed on either the inner or outer side of cushion body sidewall 32. That is, at least one stiffener passage 22 is not a through hole. Membrane 76 prevents insert 50 from exiting at least one stiffener passage 22 through one side of cushion body sidewall 32. Retaining device 70 may also be a stop 78 within at least one stiffener passage 22 and disposed adjacent the inner or outer side of cushion body sidewall 32. Stop 78 may be a protrusion that extends into at least one stiffener passage 22 such as a hemisphere or ball 80. In this exemplary embodiment, each insert 50 may include a detent 82 structured to be engaged by ball 80. Alternatively, stop 78 may be a tab 84 that extends partially over one opening 60, 62. Tab 84 may be unitary with cushion body 20 and, as such, is flexible. Tab 84 is deflected while insert 50 is placed in at least one stiffener passage 22. After insert 50 is placed in at least one stiffener passage 22, tab 84 again extends partially over one opening 60, 62 thereby trapping insert 50 in at least one stiffener passage 22.

Accordingly, a method of using mask 10 and cushion 15 described above includes the steps of inserting 200 one insert 50 in each at least one stiffener passage 22, and, positioning 202 mask 10 over the user's face. More specifically, step of inserting 200 one insert 50 in each at least one stiffener passage 22 includes the steps of determining 210 if mask 10 is providing a generally continuous seal between the user's face and cushion 15, determining 212 the location of a gap in the generally continuous seal, placing 214 insert 50 of a different material in an at least one stiffener passage 22 adjacent the location of a gap, and determining 216 if the gap has been reduced, thereby providing a more complete seal between the user's face and cushion 15. Of course, if the gap has not been reduced, or has increased, the user may simply reinsert the original insert 50.

When cushion 15 includes a plurality of stiffener passages 22, the step of inserting 200 one insert 50 in each at least one stiffener passage 22 includes the steps of placing 220 insert 50 of a first material in each stiffener passage 22, determining 222 if mask 10 is providing a generally continuous seal between the user's face and cushion 15, determining 224 the location of a gap in the generally continuous seal, placing 226 insert 50 of a second material in at least one stiffener passage 22 adjacent the location of a gap, and determining 228 if the gap has been reduced thereby providing a more complete seal between the user's face and cushion 15. If the gap has not been reduced thereby providing a more complete seal between the user's face and cushion 15 the user may reinstall inserts 50 of a first material in stiffener passages 22 having an insert 50 of the second material, or, if there are inserts 50 made from a third material having a third hardness, the user may replace inserts 50 of either the first or second hardness with inserts 50 of a third hardness.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A support cushion for a respiratory interface, the interface having a cross-sectional shape similar to the interface peripheral contour, the cushion comprising:
a cushion body and at least two inserts, the cushion body having a cross-sectional shape similar to the mask peripheral contour, the cushion body defining a passage, the cushion body comprising:
a distal member,
a sidewall, and
a proximal member, the cushion body distal member and cushion body proximal member are maintained in a spaced relation by the cushion body sidewall, the cushion body sidewall having an inner side and an outer side, the cushion body sidewall having at least one stiffener passage with an opening, wherein the at least one stiffener passage is one of an axial stiffener passage with an opening adjacent both distal member and the proximal member, or a radial stiffener passage with an opening in one of the cushion body inner side or the cushion body outer side, wherein the at least two inserts are shaped to correspond to the at least one stiffener passage, wherein the cushion body is made from a first material having a cushion body hardness, wherein the at least two inserts are made from either the first material having the first hardness, or, a second material having a second hardness, wherein the second hardness is different than the first hardness, and wherein one insert may be inserted into each of the stiffener passages and wherein selection of the insert as being of the first material or the second material selectively determines the localized hardness of the cushion.

2. The support cushion of claim 1, wherein the at least one stiffener passage has a general cross-sectional shape selected from the group including circular, oval, hexagonal, rhombus, and wave.

3. The support cushion of claim 2, wherein: the at least one stiffener passage includes a plurality of stiffener passages; each stiffener passage has generally the same shape as any other stiffener passage.

4. The support cushion of claim 1, wherein one of the at least two inserts being made from the first material having a first indicia and the other of the at least two inserts being made from the second material having a second indicia.

5. The support cushion of claim 1, wherein at least one stiffener passage is a through hole.

6. The support cushion of claim 1, wherein the cushion body includes a sealing flap, the sealing flap being coupled to the cushion body.

7. The support cushion of claim 1, wherein the cushion body includes an insert retaining device.

8. The support cushion of claim 7, wherein the cushion body includes a sealing flap, the sealing flap being coupled to the cushion body, and wherein the sealing flap includes at least one retaining band, the retaining band extending over one of the inner side of cushion body sidewall or the outer side of cushion body sidewall, the retaining band being the insert retaining device.

9. The support cushion of claim 8, wherein:
the sealing flap includes the at least one retaining band;
the at least one retaining band includes an inner retaining band and an outer retaining band, the inner retaining band extending over the cushion body sidewall inner side; and
the outer retaining band extending over the cushion body sidewall outer side.

10. The support cushion of claim 7, wherein the insert retaining device is a retaining band, the retaining band extending over the cushion body sidewall outer side.

11. The support cushion of claim 7, wherein the at least one stiffener passage is tapered.

12. The support cushion of claim 11, wherein each tapered at least one stiffener passage has a smaller cross-sectional area adjacent the cushion body inner side.

13. The support cushion of claim 7, wherein the insert retaining device is an insert stop disposed within the at least one stiffener passage.

14. The support cushion of claim 7, wherein the insert retaining device is a membrane extending over the cushion body inner side.

15. The support cushion of claim 1, wherein the at least one stiffener passage includes a plurality of passages which extend substantially about the cushion body sidewall.

16. The support cushion of claim 1, wherein the at least one stiffener passage extends generally axially.

17. The support cushion of claim 1, wherein the at least one stiffener passage extends generally radially.

18. A method of using a support cushion for a respiratory interface device mask, the mask having a faceplate with a peripheral contour, the cushion including a cushion body and at least two inserts, the cushion body having a cross-sectional shape similar to the mask peripheral contour, the cushion body defining a passage, the cushion body having an distal member, a sidewall, and a proximal member wherein the cushion body distal member and cushion body proximal member are maintained in a spaced relation by the cushion body sidewall, the cushion body sidewall having an inner side and an outer side, the cushion body sidewall having at least one stiffener passage with an opening, wherein the at least one stiffener passage is one of an axial stiffener passage with an opening adjacent both distal member and the proximal member, or a radial stiffener passage with an opening in one of the cushion body inner side or the cushion body outer side, the at least two inserts shaped to correspond to the at least one stiffener passage, the cushion body made from a first material having a cushion body hardness, the at least two inserts made from either the first material, or, a second material having a second hardness, the second hardness being different than the first hardness, wherein one insert may be inserted into each of the at least one stiffener passages and wherein selection of the insert as being of the first material or the second material selectively determines the localized hardness of the cushion, the method including the steps of:

selectively inserting one insert in each at least one axial stiffener passage through the opening in one of the distal member or the proximal member, or, in at least one radial stiffener passage through the opening in one of the cushion body inner side or the cushion body outer side; and positioning the mask over the user's face.

19. The method of claim 18, wherein the step of inserting one insert in each at least one stiffener passage includes the steps of:

determining if the mask is providing a generally continuous seal between the user's face and the cushion;

determining the location of a gap in the generally continuous seal;

placing an insert of a different material in an at least one stiffener passage adjacent the location of a gap; and determining if the gap has been reduced thereby providing a more complete seal between the user's face and the cushion.

20. The method of claim 18, wherein the at least one stiffener passage includes a plurality of stiffener passages and wherein the step of inserting one insert in each at least one stiffener passage includes the steps of:

placing an insert of a first material in each stiffener passage;

determining if the mask is providing a generally continuous seal between the user's face and the cushion;

determining the location of a gap in the generally continuous seal;

placing an insert of a second material in an at least one stiffener passage adjacent the location of a gap;

determining if the gap has been reduced thereby providing a more complete seal between the user's face and the cushion.

\* \* \* \* \*